US011326938B2

(12) United States Patent
Mo et al.

(10) Patent No.: US 11,326,938 B2
(45) Date of Patent: May 10, 2022

(54) BIO ILLUMINANCE MEASURING DEVICE FOR DETERMINING CIRCADIAN ACTION

(71) Applicant: KOOKMIN UNIVERSITY INDUSTRY ACADEMY COOPERATION FOUNDATION, Seoul (KR)

(72) Inventors: Hyun Sun Mo, Seoul (KR); Dae Jeong Kim, Seoul (KR)

(73) Assignee: KOOKMIN UNIVERSITY INDUSTRY ACADEMY COOPERATION FOUNDATION, Seoul (KR)

( * ) Notice: Subject to any disclaimer, the term of this patent is extended or adjusted under 35 U.S.C. 154(b) by 442 days.

(21) Appl. No.: 16/525,190

(22) Filed: Jul. 29, 2019

(65) Prior Publication Data
US 2020/0232844 A1 Jul. 23, 2020

(30) Foreign Application Priority Data
Jan. 23, 2019 (KR) .......................... 10-2019-0008809

(51) Int. Cl.
*G01J 1/02* (2006.01)
*G01J 1/24* (2006.01)
(Continued)

(52) U.S. Cl.
CPC .......... *G01J 1/0238* (2013.01); *A61B 5/0059* (2013.01); *G01J 1/0219* (2013.01); *G01J 1/0492* (2013.01);
(Continued)

(58) Field of Classification Search
CPC .... A61M 2205/587; A61M 2205/3306; A61M 21/00; A61M 21/02; G01J 1/0238;
(Continued)

(56) References Cited

U.S. PATENT DOCUMENTS

2011/0064098 A1* 3/2011 Omori ................... H01S 5/0427
372/29.015
2016/0027282 A1* 1/2016 Lee ......................... A61B 5/681
340/573.1

(Continued)

FOREIGN PATENT DOCUMENTS

| KR | 1020010090519 | 10/2001 |
|---|---|---|
| KR | 1020170123065 A | 11/2017 |

OTHER PUBLICATIONS

Oh et al., "Healthy, natural, efficient and tunable lighting: four-package white LEDs for optimizing the circadian effect, color quality, and vision performance," Light Sci. Appl., 3, e141, 2014 (Year: 2014).*

(Continued)

*Primary Examiner* — Jennifer D Bennett
(74) *Attorney, Agent, or Firm* — K&L Gates LLP

(57) ABSTRACT

Disclosed is a bio illuminance measuring apparatus including a circadian lambda filter passing external light along according to a circadian rhythm sensitivity curve, a visual lambda filter passing the external light along according to a visual sensitivity curve, a photo sensing portion sensing and converting the external light, which has passed through the circadian lambda filter, into a circadian wavelength signal and sensing and converting the external light, which has passed through the visual lambda filter, into a visual wavelength signal, and an illuminance calculating portion which calculates a ratio between the circadian wavelength signal and the visual wavelength signal, calculates a circadian action factor by applying the ratio between the circadian wavelength signal and the visual wavelength signal to a circadian action function which varies according to the visual wavelength signal, and calculates a bio illuminance (Continued)

value of the external light on the basis of the circadian action factor.

12 Claims, 7 Drawing Sheets

(51) Int. Cl.
*A61B 5/00* (2006.01)
*G01J 1/04* (2006.01)
*G01J 1/16* (2006.01)
*G01J 1/44* (2006.01)

(52) U.S. Cl.
CPC .............. *G01J 1/1626* (2013.01); *G01J 1/24* (2013.01); *G01J 2001/444* (2013.01)

(58) Field of Classification Search
CPC ...... G01J 1/24; G01J 2001/444; G01J 1/0492; G01J 1/626; G01J 1/4204; G01J 1/0219; H05B 33/08; A61B 5/0059; A61B 5/742; A61B 5/4836; A61B 5/4857; A61N 2005/0626; A61N 2005/0662
See application file for complete search history.

(56) References Cited

U.S. PATENT DOCUMENTS

2017/0328767 A1\* 11/2017 Zheng .................. G09G 3/2092
2018/0339127 A1\* 11/2018 Van Reen ............ A61N 5/0618
2020/0230346 A1\* 7/2020 Mo ...................... A61N 5/0618

OTHER PUBLICATIONS

Koran Office Action for related Korean Application No. 10-2019-0008809; action dated May 18, 2020; (4 pages).

\* cited by examiner

BIO ILLUMINANCE MEASURING DEVICE FOR DETERMINING CIRCADIAN ACTION

CROSS-REFERENCE TO RELATED APPLICATION

This application claims priority to and the benefit of Korean Patent Application No. 2019-0008809, filed on Jan. 23, 2019, the disclosure of which is incorporated herein by reference in its entirety.

BACKGROUND

1. Field of the Invention

The present invention relates to a bio illuminance measuring apparatus, and more particularly, to a bio illuminance measuring apparatus capable of calculating a more precise bio illuminance value.

2. Discussion of Related Art

A human being lives having a cycle of a single day, which is referred to as a circadian rhythm. The circadian rhythm is most influenced by light.

On the basis of the sun, a variety of living things have been altered and adapted together according to a daily change of the sun in which it becomes increasingly brighter as the sun rises in the morning and becomes increasingly darker as the sun sets in the evening. Also, human beings have lived having a cycle in a single day while being influenced by a daily cycle of the sun, by getting up as the sun rises to start the day and taking a rest and sleeping as the sun sets.

Meanwhile, when light is received in the evening time period, a secretion of melatonin, which is one hormone having a great effect on sleep of our bodies, is suppressed such that sound sleep is disturbed and a probability of being exposed to a variety of diseases is increased.

Diseases caused by a disturbance in a circadian rhythm include seasonal affective disorder, somnipathy, depression, fatigue caused by time difference, health conditions related to shift work, and the like. To cure the diseases, it is necessary to allow circadian rhythm to be balanced well by promoting smooth melatonin secretion in the evening time period by suppressing melatonin secretion in the morning time period.

Meanwhile, general illuminance measuring apparatuses measure illuminance Lux of external light using a visual lambda V($\lambda$) filter according to a photo sensing property curve with respect to human eyes, that is, a visual sensitivity curve. Here, the illuminance Lux means intensity of light which is recognizable by human eyes and will be referred to as visual illuminance Lux hereinafter to be distinguished from bio illuminance Biolux which will be described.

According to the visual sensitivity curve, light having a wavelength band of 380 nm to 780 nm has a maximum sensitivity.

However, when a general illuminance measuring apparatus according to the visual sensitivity curve measures a visual illuminance value without correction with respect to different types of external light, a bio illuminance value having an effect on a circadian rhythm of a human may vary according to a type of an external light source.

This is because an emission spectrum varies according to the type of the external light source, and a photo sensing property with respect to hormones which control the circadian rhythm also varies when the emission spectrum varies.

For the same reason, in order to measure bio illuminance, it is important to detect a color temperature of the external light source or circadian action factor (CAF) information.

However, in order to obtain the above information, it is necessary to use an expensive reference spectrometer and there is a limitation in miniaturization due to properties of a sensor and a detector.

RELATED ART DOCUMENT

Patent Document

Korean Patent Publication No. 10-2001-0090519

SUMMARY OF THE INVENTION

The present invention is directed to providing a bio illuminance measuring apparatus capable of measuring a circadian action factor and bio illuminance using a relatively simple method by applying a circadian lambda filter and a visual lambda filter thereto, being miniaturized by omitting an additional component for calculating the bio illuminance, and being applicable to a variety of products at a low cost.

The present invention is also directed to providing a bio illuminance measuring apparatus capable of calculating a bio illuminance value by reflecting a circadian action function, which varies for each visual wavelength signal, and a circadian action factor to calculate an accurate bio illuminance value.

The present invention is also directed to providing a bio illuminance measuring apparatus capable of diagnosing a circadian rhythm of a user by measuring bio illuminance and reinforcing the circadian rhythm of the user according to a diagnosis result.

Technical objectives of the present invention are not limited to the above technical objectives and additional unstated technical objectives will be clearly understood by one of ordinary skill in the art from the following description.

According to an aspect of the present invention, there is provided a bio illuminance measuring apparatus including a circadian lambda filter which passes along external light according to a circadian rhythm sensitivity curve, a visual lambda filter which passes along the external light according to a visual sensitivity curve, a photo sensing portion that senses and converts the external light, which has passed through the circadian lambda filter, into a circadian wavelength signal and senses and converts the external light, which has passed through the visual lambda filter, into a visual wavelength signal, and an illuminance calculating portion which calculates a ratio between the circadian wavelength signal and the visual wavelength signal, calculates a circadian action factor by applying the ratio between the circadian wavelength signal and the visual wavelength signal to a circadian action function which varies according to the visual wavelength signal, and calculates a bio illuminance value of the external light on the basis of the circadian action factor.

The illuminance calculating portion may include a function storage which stores a plurality of circadian action functions which vary according to each of certain ranges of the visual wavelength signal.

The illuminance calculating portion may further include a function caller which calls a function corresponding to the visual wavelength signal among the plurality of circadian action functions stored in the function storage.

The circadian action function may be a function which defines a relation between the circadian action factor and the ratio between the circadian wavelength signal and the visual wavelength signal. Here, the ratio between the circadian wavelength signal and the visual wavelength signal may become an independent variable, and the circadian action factor may become a dependent variable.

The circadian action factor may be proportional to the ratio between the circadian wavelength signal and the visual wavelength signal.

The illuminance calculating portion may include a visual illuminance calculator which calculates a visual illuminance value of the external light on the basis of the visual wavelength signal.

The bio illuminance value may be calculated by multiplying the circadian action factor by the visual illuminance value.

The photo sensing portion may include a first photo diode that senses the external light, which has passed through the circadian lambda filter, and outputs a circadian wavelength current, a second photo diode that senses the external light, which has passed through the visual lambda filter, and outputs a visual wavelength current, and a third photo diode at which the external light is blocked and which outputs a dark current.

The photo sensing portion may further include a first variable resistor which converts the circadian wavelength current into a circadian wavelength voltage, a second variable resistor which converts the visual wavelength current into a visual wavelength voltage, and a third variable resistor which converts the dark current into a dark voltage.

The circadian wavelength signal may be a first analog signal corresponding to a difference between the circadian wavelength voltage and the dark voltage, and the visual wavelength signal may be a second analog signal corresponding to a difference between the visual wavelength voltage and the dark voltage.

The bio illuminance measuring apparatus may further include a controller which adjusts a voltage gain value with respect to the external light by varying resistance values of the first to third variable resistors and converts the first and second analog signals into digital signals.

The bio illuminance measuring apparatus may further include a display portion which displays the bio illuminance value and the visual illuminance value.

The circadian rhythm sensitivity curve may be a photo sensing property curve with respect to hormones, which control a circadian rhythm, and may have a maximum sensitivity in a circadian wavelength band.

The hormones which control the circadian rhythm may be melatonin or cortisol.

The circadian wavelength band may be 400 nm to 600 nm.

The visual sensitivity curve may be a photo sensing property curve with respect to human eyes and may have a maximum sensitivity in a visual wavelength band.

The visual wavelength band may be 380 nm to 780 nm.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
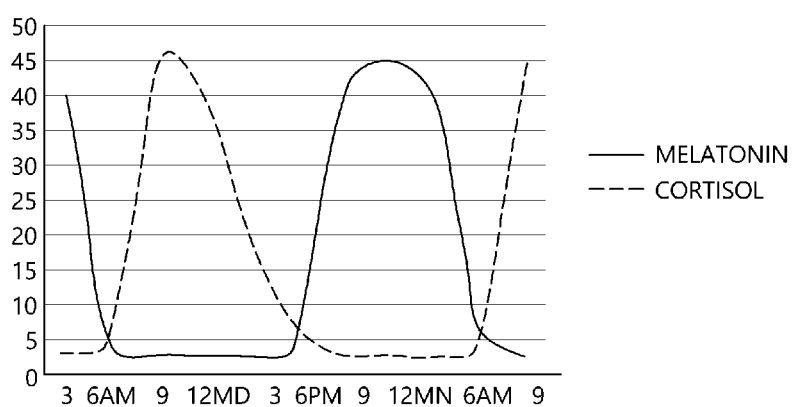
FIG. 1 is a graph illustrating melatonin and cortisol secretion rates according to a daily cycle of a human.

Exemplary embodiments according to the present invention will be described in detail with reference to the attached drawings. Regardless of signs in drawings, equal or similar elements will be referred to with like reference numerals and an overlapped description thereof will be omitted.

Also, in the description of the embodiments of the present invention, a detailed description of a well-known technology of the related art will be omitted when it is deemed to obscure the essence of the present invention. Also, it should be noted that the attached drawings are merely for allowing the concept of the present invention to be easily understood and the concept of the present invention is not to be construed as being limited to the attached drawings.

FIG. 1 is a graph illustrating melatonin and cortisol secretion rates according to a daily cycle of a human.

As shown in FIG. 1, it may be seen that a melatonin secretion amount is very low from 6 a.m. to 6 p.m. and rapidly increases from 6 p.m., is at a maximum value at midnight, and is rapidly reduced until 6 a.m.

Also, on the contrary to melatonin, it may be seen that a cortisol secretion rate is very low from 6 p.m. to 6 a.m., rapidly increases from 6 a.m., is at a maximum value at noon, and is rapidly reduced until 6 p.m.

As described above, a bio illuminance measuring apparatus according to an embodiment of the present invention measures a bio illuminance value Biolux using hormones such as melatonin and cortisol, which control a circadian rhythm of a human, as relating to light.

Figure 2:
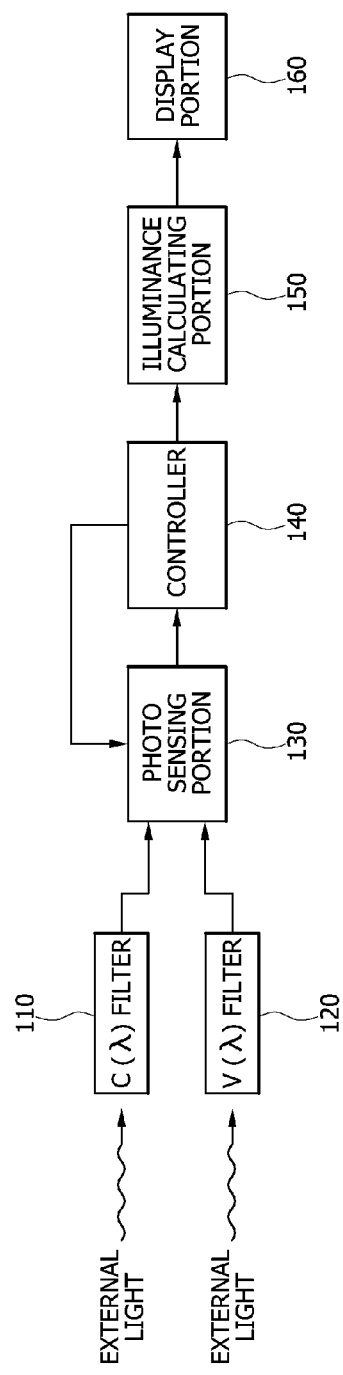
FIG. 2 is a schematic block diagram of a bio illuminance measuring apparatus according to an embodiment of the present invention.

FIG. 2 is a schematic block diagram of a bio illuminance measuring apparatus according to an embodiment of the present invention. Also, FIG. 3 is a graph illustrating a circadian rhythm sensitivity curve and a visual sensitivity curve;

As shown in FIG. 2, the bio illuminance measuring apparatus according to the embodiment of the present invention may include a circadian lambda filter (C(λ) filter) 110, a visual lambda filter (V(λ) filter) 120, a photo sensing portion 130, a controller 140, an illuminance calculating portion 150, and a display portion 160.

The circadian lambda filter 110 passes external light along according to a circadian rhythm sensitivity curve.

Figure 3:
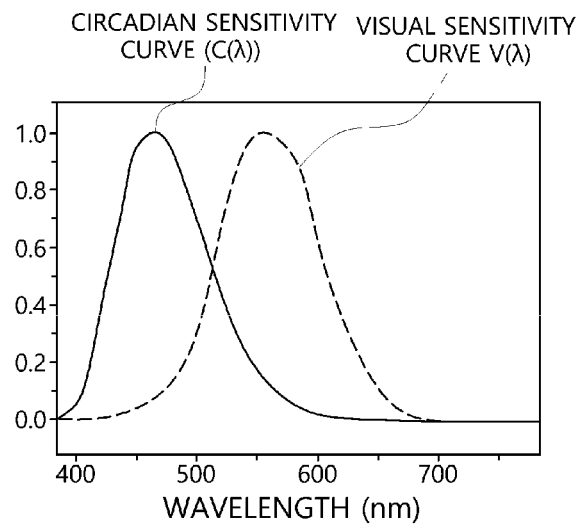
FIG. 3 is a graph illustrating a circadian rhythm sensitivity curve and a visual sensitivity curve.

As shown in FIG. 3, the circadian rhythm sensitivity curve is a photo sensing property curve with respect to hormones (for example, melatonin or cortisol) which control the circadian rhythm of the human and has a maximum sensitivity at a circadian wavelength band. Here, the circadian wavelength band may be 400 nm to 600 nm.

According to the circadian rhythm sensitivity curve, light having a wavelength band of 400 nm to 600 nm has a maximum sensitivity.

Accordingly, the circadian lambda filter 110 according to the circadian rhythm sensitivity curve operates as a band pass filter which passes along external light having a wavelength of 400 nm to 600 nm which is the circadian wavelength band and blocks external light having other wavelength bands.

Also, the circadian lambda filter 110 transmits light having a wavelength of 400 nm to 600 nm and has a maximum transmittance at a wavelength band of about 450 nm.

The visual lambda filter 120 passes along external light according to a visual sensitivity curve.

As shown in FIG. 3, the visual sensitivity curve is a photo sensing property curve with respect to human eyes and is a curve having a maximum sensitivity in a visual wavelength band. Here, the visual wavelength band may be 450 nm to 700 nm.

According to the visual sensitivity curve, light having a wavelength band of 450 nm to 700 nm has a maximum sensitivity.

Accordingly, the visual lambda filter 120 according to the visual sensitivity curve operates as a band pass filter which passes along external light having a wavelength of 450 nm to 700 nm, which is the visual wavelength band, and blocks external light having other wavelength bands.

Figure 4:
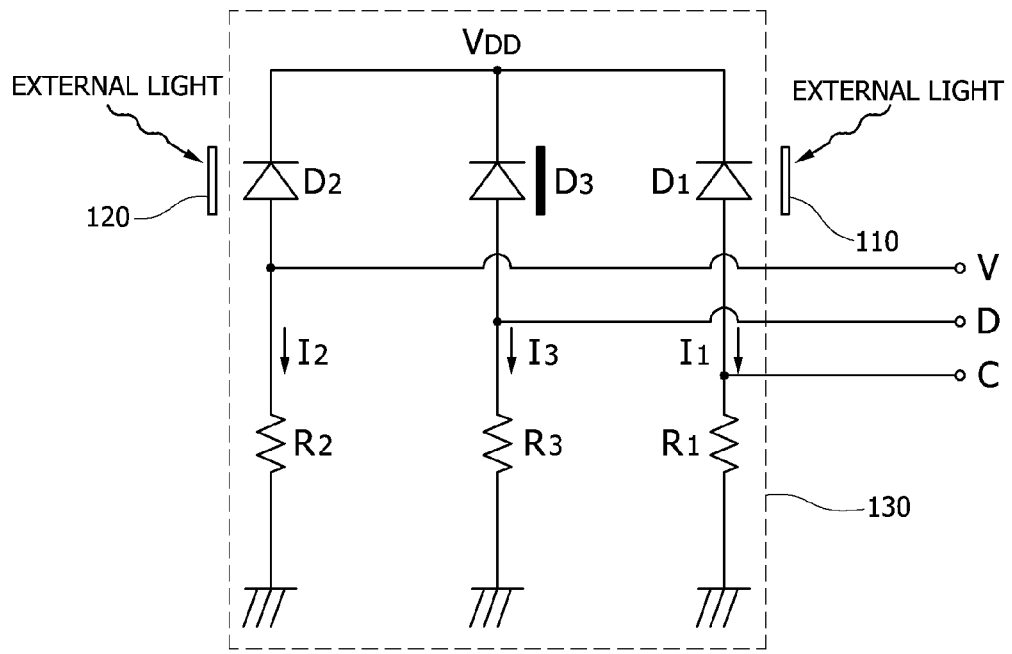
FIG. 4 is a detailed circuit diagram illustrating a photo sensing portion shown in FIG. 2.

FIG. 4 is a detailed circuit diagram illustrating the photo sensing portion shown in FIG. 2.

As shown in FIG. 4, the photo sensing portion 130 senses external light which has passed through the circadian lambda filter 110, converts the external light into a circadian wavelength signal C (for example, a voltage value), senses external light which has passed through the visual lambda filter 120, converts the external light into a visual wavelength signal V (for example, a voltage value), and outputs the visual wavelength signal V.

Here, the photo sensing portion 130 may include first to third photo diodes D1 to D3 and first to third variable resistors R1 to R3 and may output values corresponding to values obtained by integrating light amounts passing through the circadian lambda filter 110 and the visual lambda filter 120 for each wavelength.

Here, the first photo diode D1 and the first variable resistor R1 are connected in series and form a first circuit, the second photo diode D2 and the second variable resistor R2 are connected in series and form a second circuit, and the third photo diode D3 and the third variable resistor R3 are connected in series and form a third circuit. Also, the first to third circuits are connected in parallel.

In detail, the first photo diode D1 senses external light which has passed through the circadian lambda filter 110 and outputs a circadian lambda current I1 corresponding thereto, the second photo diode D2 senses external light which has passed through the visual lambda filter 120 and outputs a visual lambda current I2 corresponding thereto, and the third photo diode D3 outputs a dark current I3 in a dark state in which external light is blocked.

Also, the first variable resistor R1 converts the circadian wavelength current I1 output from the first photo diode D1 into a circadian wavelength voltage VC, the second variable resistor R2 converts the visual wavelength current I2 output from the second photo diode D2 into a visual wavelength voltage VV, and the third variable resistor R3 converts the dark current I3 output from the third photo diode D3 into a dark voltage VD.

That is, a voltage applied to both ends of the first variable resistor R1 becomes the circadian wavelength voltage VC, a voltage applied to both ends of the second variable resistor R2 becomes the visual wavelength voltage VV, and a voltage applied to both ends of the variable resistor R3 becomes the dark voltage VD.

Here, the circadian wavelength signal C is a first analog signal corresponding to a difference between the circadian wavelength voltage VC and the dark voltage VD, and the visual wavelength signal VV is a second analog signal corresponding to a difference between the visual wavelength voltage VV and the dark voltage VD.

That is, the circadian wavelength signal C may be defined by the following Equation 1, and the visual wavelength signal V may be defined by the following Equation 2.

$$C=(I1 \times R1)-(I3 \times R3)=VC-VD \quad \text{[Equation 1]}$$

$$V=(I2 \times R2)-(I3 \times R3)=VV-VD \quad \text{[Equation 2]}$$

As described above, the photo sensing portion 130 of the bio illuminance measuring apparatus according to the embodiment of the present invention may remove self-generated noise inherent in a photo diode by calculating the circadian wavelength signal C and the visual wavelength signal V as differential voltages obtained by deducting the dark voltages VD from the circadian wavelength voltage VC and visual wavelength voltage VV so as to precisely sense the circadian wavelength signal C and the visual wavelength signal V therethrough.

The controller 140 may receive the circadian wavelength signal C and the visual wavelength signal V, which are analog signals output by the photo sensing portion 130, that is, the first analog signal and the second analog signal, may convert the circadian wavelength signal C and the visual wavelength signal V into digital signals, and may output the digital signals to the illuminance calculating portion 150.

Here, the controller 140 may adjust a voltage gain value with respect to external light by varying resistance values of the first to third variable resistors R1 to R3. That is, when the digital signals obtained by conversion deviate from a processible range of the illuminance calculating portion 150 and become saturated, the controller 140 reduces the resistance values of the first to third variable resistors R1 to R3 by outputting a control signal to the photo sensing portion 130 such that the photo sensing portion 130 outputs a first analog signal C and a second analog signal V within a range processible by the illuminance calculating portion 150.

Figure 5:
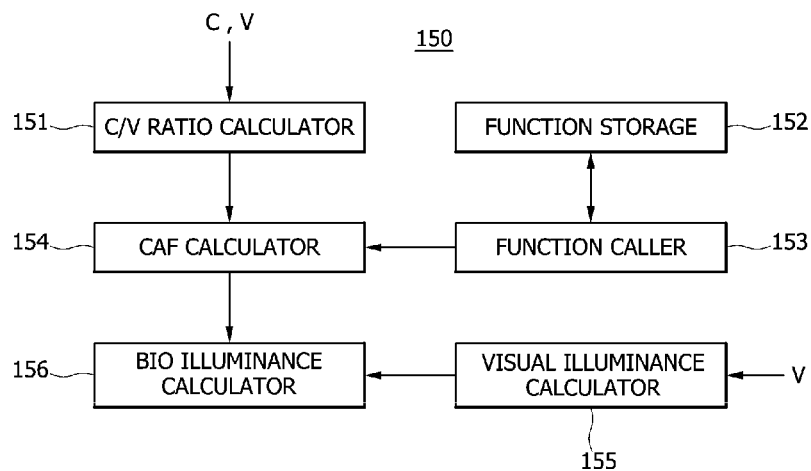
FIG. 5 is a detailed block diagram illustrating an illuminance calculating portion shown in FIG. 2.

FIG. 5 is a detailed block diagram illustrating the illuminance calculating portion shown in FIG. 2.

As shown in FIG. 5, the illuminance calculating portion 150 may include a C/V ratio calculator 151, a function storage 152, a function caller 153, a circadian action factor (CAF) calculator 154, a visual illuminance calculator 155, and a bio illuminance calculator 156.

The C/V calculator 151 receives the circadian wavelength signal C and the visual wavelength signal V from the controller 140 or the photo sensing portion 130 and calculates a ratio (C/V ratio) between the circadian wavelength signal C and the visual wavelength signal V.

The CAF calculator 154 calculates a CAF on the basis of the ratio (C/V ratio) between the circadian wavelength signal C and the visual wavelength signal V.

Here, the CAF may be defined as a ratio of circadian efficacy of radiation (CER) with respect to luminous efficacy of radiation (LER).

Figure 6:
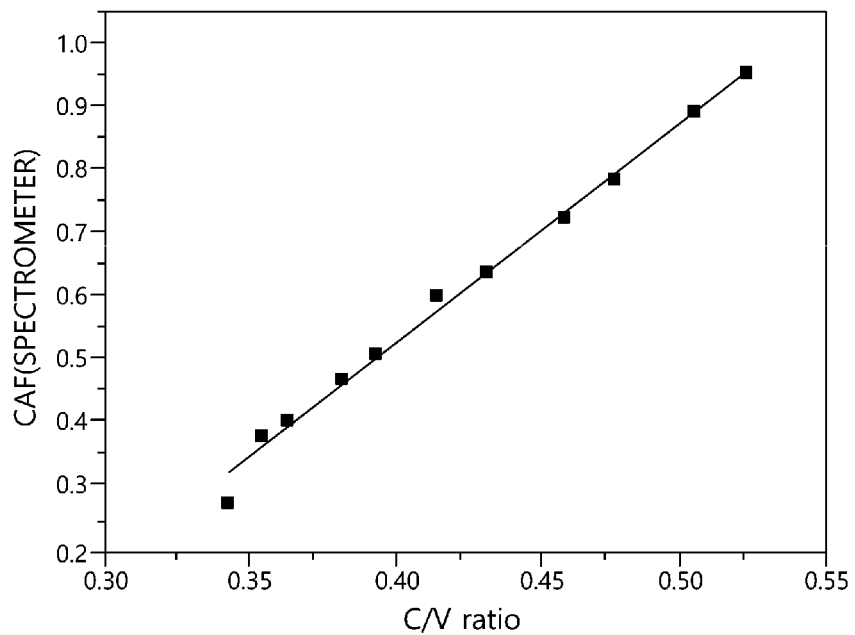
FIG. 6 is a graph illustrating a relation between a reference circadian action factor (CAF) and a C/V ratio.

FIG. 6 is a graph illustrating a relation between a reference CAF and a C/V ratio.

Here, a reference CAF was measured using an additional reference spectrometer, and a ratio (C/V ratio) of a circadian wavelength signal C to a visual wavelength signal V was measured by the C/V ratio calculator 151 of the present invention.

As shown in FIG. 6, it may be seen that the ratio (C/V ratio) of the circadian wavelength signal C to the visual wavelength signal V is linearly proportional to the reference CAF.

FIG. 7 is a graph illustrating a relation between a CAF and a C/V ratio, which varies according to a visual wavelength signal.

Here, the C/V ratio calculator 151 of the present invention calculated a ratio (C/V ratio) of a circadian wavelength signal C to a visual wavelength signal V with respect to external light having a different color temperature, which was shown for each color temperature in the graph. Also, an additional reference spectrometer (not shown) measured a reference CAF with respect to each of other types of external light which have different color temperatures, and the reference CAF was shown for each color temperature in the drawings.

As shown in FIG. 7, it may be seen that the reference CAF and the ratio (C/V ratio) of the circadian wavelength signal C to the visual wavelength signal V are proportional to the color temperature of external light.

Also, it may be seen that a certain functional relation is present between the CAF and the ratio (C/V ratio) of the circadian wavelength signal C to the visual wavelength signal V. Also, the relation may be defined by the following Equation 3.

$$\text{CAF} = F(C/V \text{ ratio}) = A \times (C/V \text{ ratio}) + B \qquad \text{[Equation 3]}$$

Here, F(C/V ratio) is a circadian action function, and A and B are certain constants and may vary according to the visual wavelength signal V. That is, referring to FIGS. 7A to 7C, the circadian action function F(C/V ratio) varies according to the visual wavelength signal V.

The circadian action function F(C/V ratio) is a function which defines the relation between the CAF and the ratio (C/V ratio) between the visual wavelength V and the circadian wavelength signal C, in which the ratio between the circadian wavelength signal C and the visual wavelength signal V is an independent variable and the CAF is a dependent variable.

Figure 7A:
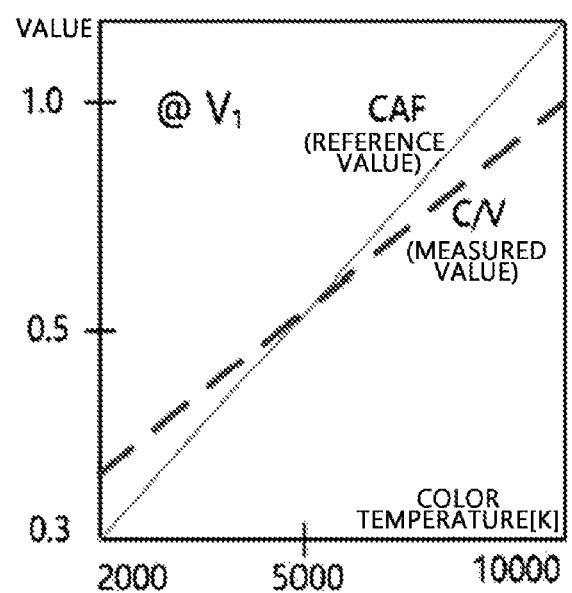
FIG. 7 is a graph illustrating a relation between a CAF and a C/V ratio, which varies according to a visual wavelength signal.
Figure 7B:
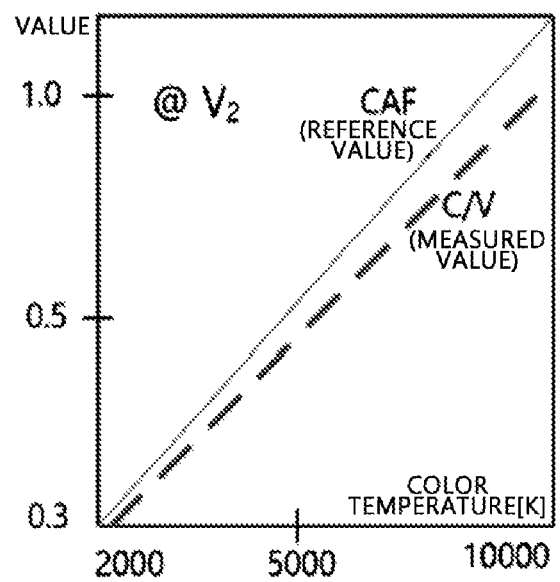
Figure 7C:
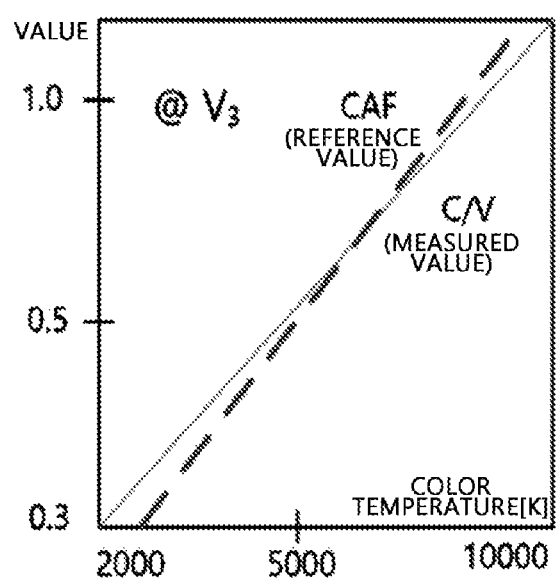

Meanwhile, V1, V2, and V3 shown in FIGS. 7A to 7C may mean representative values among visual wavelength signals V within a certain range. Here, the circadian action function F(C/V ratio) may vary for each certain range of the visual wavelength signal V.

The function storage 152 stores a plurality of circadian action functions F(C/V ratios) which vary for each certain range of the visual wavelength signal V.

The function caller 153 calls a function corresponding to the visual wavelength signal V input from the photo sensing portion 130 or the controller 140 among the plurality of circadian action functions F(C/V ratios) stored in the function storage 152.

The CAF calculator 154 calculates the CAF by applying the C/V ratio calculated by the C/V calculator 151 to the circadian action function F(C/V ratio) called by the function caller 153.

The bio illuminance calculator 156 calculates a bio illuminance value Biolux of external light on the basis of the CAF.

Figure 8:
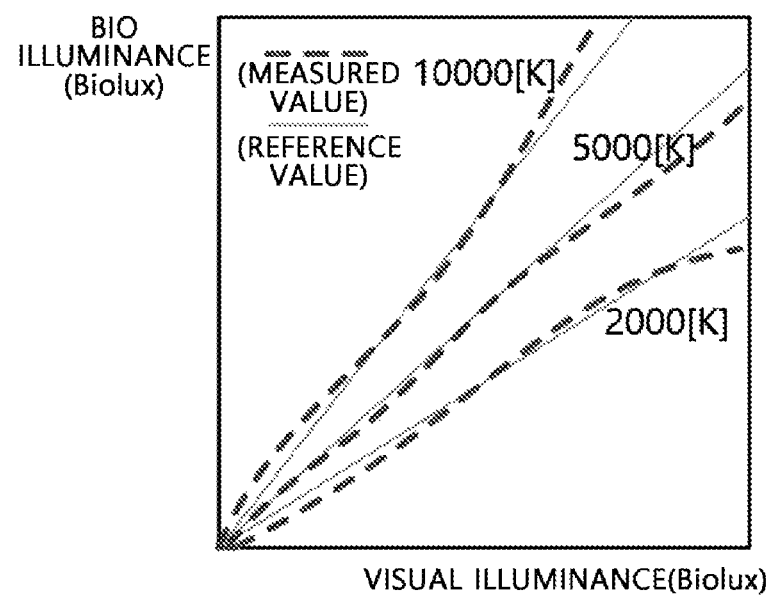
FIG. 8 is a graph illustrating a relation between visual illuminance and bio illuminance.

FIG. 8 is a graph illustrating a relation between visual illuminance and bio illuminance.

As shown in FIG. 8, visual illuminance Lux and bio illuminance Biolux are directly proportional to each other, and a proportional constant thereof is a CAF. Also, the relation between the visual illuminance Lux and bio illuminance Biolux varies according to a color temperature of external light, and the CAF is a function of the color temperature of the external light and increases as the color temperature increases.

Accordingly, the bio illuminance Biolux may be defined by the following Equation 4.

$$\text{Biolux} = \text{CAF} \times \text{Lux} \qquad \text{[Equation 4]}$$

The illuminance calculating portion 150 may be divided into the visual illuminance calculator 155 and the bio illuminance calculator 156.

Here, the visual illuminance calculator 155 receives the visual wavelength signal V and calculates a visual illuminance value Lux on the basis thereof, and the bio illuminance calculator 156 receives the CAF from the CAF calculator 154 and calculates a bio illuminance value Biolux of external light on the basis of the CAF.

In detail, the bio illuminance calculator 156 receives the visual illuminance value Lux from the visual illuminance calculator 155 and calculates the bio illuminance value Biolux by multiplying the visual illuminance value Lux by the CAF.

The display portion 160 displays the visual illuminance value Lux and the bio illuminance value Biolux calculated by the illuminance calculating portion 150.

The display portion 160 may display a light exposure environment that affects the circadian rhythm, thereby indirectly warn the user that the circadian rhythm is broken, and may correct the circadian rhythm of the user according to the light exposure environment.

Through this, the user may be allowed to visually check a present circadian rhythm state of the user and to correct the circadian rhythm according to the circadian rhythm state.

As described above, the illuminance measuring apparatus according to the embodiment of the present invention may measure the bio illuminance value Biolux using a relatively simple method in comparison to a conventional method by directly calculating the CAF using the circadian lambda filter 110 and the visual lambda filter 120 and calculating the bio illuminance value Biolux on the basis thereof.

Also, since the bio illuminance value Biolux is calculated by reflecting the CAF and the circadian action function F(C/V ratio) which varies for each visual wavelength signal, it is possible to calculate a precise bio illuminance value Biolux.

Also, since it is possible to omit an additional component for calculating the bio illuminance value Biolux, the bio illuminance measuring apparatus may be miniaturized and is applicable to a variety of products at a low cost.

Also, the bio illuminance measuring apparatus according to the embodiment of the present invention may indirectly measure a light exposure environment and may reinforce the circadian rhythm of the user by using an additional circadian rhythm reinforcing portion (not shown) according to the light exposure environment.

That is, it is possible to correct a distorted circadian rhythm of the user by adjusting hormones which control the circadian rhythm, and it is possible to cure diseases caused by a disturbance in the circadian rhythm, for example, a seasonal affective disorder, somnipathy, depression, fatigue caused by time difference, and health conditions related to shift work.

For example, melatonin secretion of a user is suppressed by emitting light of a circadian wavelength band toward user's eyes in the morning time period through the circadian rhythm reinforcing portion such that user's circadian rhythm may be well balanced by allowing melatonin secretion to be easily performed in the night time period.

Also, the bio illuminance measuring apparatus according to the embodiment of the present invention may further include a storage portion (not shown) which stores a circadian rhythm according to a time flow and a necessary reference bio illuminance value according to the circadian rhythm.

Here, the reference bio illuminance value stored in the storage portion and the measured bio illuminance value Biolux are compared. When the measured bio illuminance value Biolux is smaller than the reference bio illuminance value, a warning for reinforcing the circadian rhythm may be displayed on the display portion 160.

Figure 9:
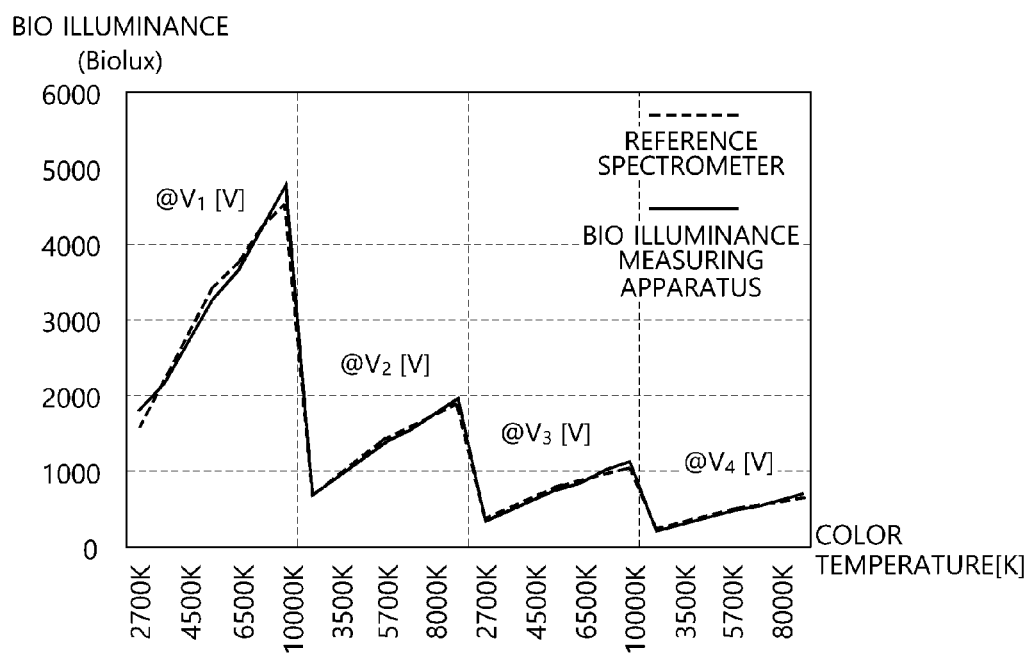
FIG. 9 is a graph illustrating a comparison between bio illuminance values measured by a bio illuminance measuring apparatus and a reference spectrometer according to the embodiment of the present invention.

FIG. 9 is a graph illustrating a comparison between bio illuminance values measured by the bio illuminance measuring apparatus according to the embodiment of the present invention and the reference spectrometer.

As shown in FIG. 9, it may be seen that the bio illuminance value Biolux measured by the illuminance measuring apparatus according to the embodiment of the present invention and the bio illuminance value Biolux measured by the reference spectrometer have approximately equal patterns. Also, it may be seen that a bio illuminance value Biolux increases in proportion to a color temperature of external light and has a different pattern according to a certain range of a visual wavelength signal V of the external light.

According to the present invention, there are present effects of measuring a circadian action factor and bio illuminance using a relatively simple method by applying a circadian lambda filter and a visual lambda filter thereto, miniaturizing a bio illuminance measuring apparatus by omitting an additional component for calculating the bio illuminance, and being applicable to a variety of products at a small cost.

Also, according to the embodiments of the present invention, an accurate bio illuminance value may be calculated by calculating a bio illuminance value by reflecting a circadian action factor and a circadian action function which varies for each visual wavelength signal.

Also, according to the embodiments of the present invention, there are effects of diagnosing circadian rhythm of a user by measuring bio illuminance and reinforcing the circadian rhythm of the user according to diagnosed circadian rhythm of the user.

The effects of the present invention are not limited to the above effects, and additional unstated effects will be clearly understood by one of ordinary skill in the art from the following description.

The embodiment described in the specification and the attached drawings are merely for describing parts of the technical concept of the present invention as an example. Accordingly, since the embodiments disclosed herein are not intended to limit but rather explain the technical concept of the present invention, it is apparent that the scope of the technical concept of the present invention is not to be limited by the above embodiments. It should be construed that modified examples and detailed embodiments easily derived by one of ordinary skill in the art without departing from the range of the technical concept included in the specification and drawings of the present invention are included in the scope of the present invention.

What is claimed is:

1. A bio illuminance measuring apparatus comprising:
   a circadian lambda filter which passes external light along according to a circadian rhythm sensitivity curve;
   a visual lambda filter which passes the external light along according to a visual sensitivity curve;
   a photo sensor that senses and converts the external light, which has passed through the circadian lambda filter, into a circadian wavelength signal corresponding to a difference between a circadian wavelength voltage and a dark voltage and senses and converts the external light, which has passed through the visual lambda filter, into a visual wavelength signal corresponding to a difference between a visual wavelength voltage and a dark voltage; and
   an illuminance calculator which calculates a ratio between the circadian wavelength signal and the visual wavelength signal, calculates a circadian action factor by applying the ratio between the circadian wavelength signal and the visual wavelength signal to a circadian action function which varies according to the visual wavelength signal, and calculates a bio illuminance value of the external light on the basis of the circadian action factor,
   wherein the illuminance calculator comprises a function storage which stores a plurality of circadian action functions which vary according to each of certain ranges of the visual wavelength signal,
   wherein the circadian wavelength signal is a first analog signal corresponding to a difference between the circadian wavelength voltage and the dark voltage, and
   wherein the visual wavelength signal is a second analog signal corresponding to a difference between the visual wavelength voltage and the dark voltage.

2. The bio illuminance measuring apparatus of claim 1, wherein the illuminance calculator further comprises a function caller which calls a function corresponding to the visual wavelength signal among the plurality of circadian action functions stored in the function storage.

3. The bio illuminance measuring apparatus of claim 1, wherein the circadian action function is a function which defines a relation between the circadian action factor and the ratio between the circadian wavelength signal and the visual wavelength signal, and
   wherein the ratio between the circadian wavelength signal and the visual wavelength signal becomes an independent variable, and the circadian action factor becomes a dependent variable.

4. The bio illuminance measuring apparatus of claim 1, wherein the circadian action factor is proportional to the ratio between the circadian wavelength signal and the visual wavelength signal.

5. The bio illuminance measuring apparatus of claim 1, wherein the illuminance calculator comprises a visual illuminance calculator which calculates a visual illuminance value of the external light on the basis of the visual wavelength signal.

6. The bio illuminance measuring apparatus of claim 5, wherein the bio illuminance value is calculated by multiplying the circadian action factor by the visual illuminance value.

7. The bio illuminance measuring apparatus of claim 1, wherein the photo sensor comprises:

a first photo diode that senses the external light, which has passed through the circadian lambda filter, and outputs a circadian wavelength current;

a second photo diode that senses the external light, which has passed through the visual lambda filter, and outputs a visual wavelength current; and a third photo diode at which the external light is blocked and which outputs a dark current.

8. The bio illuminance measuring apparatus of claim 7, wherein the photo sensing portion further comprises:

a first variable resistor which converts the circadian wavelength current into the circadian wavelength voltage;

a second variable resistor which converts the visual wavelength current into the visual wavelength voltage; and a third variable resistor which converts the dark current into the dark voltage.

9. The bio illuminance measuring apparatus of claim 8, further comprising a controller which adjusts a voltage gain value with respect to the external light by varying resistance values of the first to third variable resistors and converts the first and second analog signals into digital signals.

10. The bio illuminance measuring apparatus of claim 6, further comprising a display which displays the bio illuminance value and the visual illuminance value.

11. The bio illuminance measuring apparatus of claim 1, wherein the circadian rhythm sensitivity curve is a photo sensing property curve with respect to hormones, which control a circadian rhythm, and has a maximum sensitivity in a circadian wavelength band.

12. The bio illuminance measuring apparatus of claim 1, wherein the visual sensitivity curve is a photo sensing property curve with respect to human eyes and has a maximum sensitivity in a visual wavelength band.

* * * * *